United States Patent [19]
Leaver et al.

[11] 4,066,879
[45] Jan. 3, 1978

[54] MEANS AND METHOD FOR CONTROLLING ELUENT GRADIENT IN LIQUID CHROMATOGRAPHY

[75] Inventors: Brian E. Leaver, Lake Park; William F. Dudley, Jr., Riviera Beach, both of Fla.

[73] Assignee: Milton Roy Company, St. Petersburg, Fla.

[21] Appl. No.: 698,278

[22] Filed: June 21, 1976

[51] Int. Cl.² .................... B01D 15/08; G01N 31/08; G06G 7/58
[52] U.S. Cl. ..................................... 364/498; 73/698; 73/61.1 C; 23/230 A; 23/253 A; 23/498; 210/198 C; 364/579
[58] Field of Search ........... 235/151.1, 151.12, 151.34, 235/151.35; 210/198 C, 31 C, 24 C; 23/232 C, 230 A, 230 R, 253 R; 73/23.1, 61.1 C

[56] References Cited
U.S. PATENT DOCUMENTS

| | | | |
|---|---|---|---|
| 3,446,057 | 5/1969 | Bakalyar et al. | 73/23.1 |
| 3,649,203 | 3/1972 | Schneider | 210/198 C X |
| 3,701,609 | 10/1972 | Bailey | 73/61.1 C X |
| 3,917,531 | 11/1975 | Magnussen | 210/198 C X |
| 3,985,019 | 10/1976 | Boehme et al. | 73/61.1 C |

*Primary Examiner*—Joseph F. Ruggiero
*Attorney, Agent, or Firm*—Woodcock, Washburn, Kurtz & Mackiewicz

[57] ABSTRACT

An apparatus and method for producing a gradient between two eluents. The form or slope characteristics of the gradient may be varied to suit a given application. Apparatus are provided for expanding or compressing the range of the gradient while maintaining its form over a wide range of values. In a preferred embodiment the apparatus include means for controlling the form of the reset gradient in order to avoid detrimental shock to the chromatographic column.

17 Claims, 4 Drawing Figures

MEANS AND METHOD FOR CONTROLLING ELUENT GRADIENT IN LIQUID CHROMATOGRAPHY

BACKGROUND OF THE INVENTION

The present invention relates to liquid chromatography, and more specifically to an improved system for controlling the rate of change characteristic, or gradient, between two eluents flowing into a liquid chromatography column.

Chromatography, broadly stated, is an analytical procedure which comprises a method for separating constitutents in a mixture, wherein it is desired to identify certain or all of the constituents. Basically, the identity of the constituents is determined by monitoring the relative transit time of the various constituents through a separation element, or column. The column is packed with a material such as a treated resin, and the sample is transported through the column by means of a mobile phase or carrier, termed an eluent. As the eluent sweeps the sample through the column, various constitutents of the sample are selectively adsorbed and desorbed by material of the column. The rate of adsorption and succeeding release of the adsorbed component into the flowing eluent, depends upon several parameters including the nature of the column material, and of the component itself. Accordingly, certain components are adsorbed and desorbed more rapidly than others, and accordingly exit at the distal end of the column at an earlier time. A sensor at the distal end of the column is responsive to the appearance of separated constituents and produces output signals indicating their passage. The transducer, however, is usually itself incapable of distinguishing among the constituents; their identity is inferred from their relative time of arrival.

It will be appreciated that in order to infer the identity of the constituents, their arrival times must not occur all at once. The "peaks" which correspond to transducer signals indicating the passage of separated constituents must be discrete in time so that each of the various constituents may be identified.

Due to the irregular nature of the adsorption/desorption characteristics of the constituents of any given sample, it often occurs that some constituents pass through the chromatograph column at approximately the same rate. Several techniques have been devised in order to separate the closely-placed peaks, without unduly expanding the length of the sample run time. Indeed, if the process is unduly lengthened the resolution or "sharpness" of the detected peaks may degenerate to such an extent that the presence of a peak is difficult to ascertain. Aside from this it is not desirable to occupy analytical equipment for lengthy periods and accordingly it is desirable to minimize run times.

One of the techniques which has been developed for separating constituent peaks in liquid chromatography is termed gradient elution. With such a process a plurality, preferably two, eluents are used to carry a sample through the sample column. The proportion of the eluents is changed as a function of time starting, for instance, with a 100% concentration of a first eluent and changing the proportion until, near the end of the run, the second eluent constitutes 100% of the eluent being used. The rate of change of the ratio between the two eluents is termed the gradient; a constant rate of change results in a linear gradient, while a variable rate of change may produce non-linear, e.g. exponential, gradients. It has been found that in many instances exponential gradients are extremely useful since, for example, an initial part of a sample run may take place with a first eluent ratio which varies only slowly; while the latter portion of the run can occur under conditions wherein the eluent ratio varies rapidly. Such changes in the eluent gradient have been found to be highly advantageous in producing the desired peak separations.

In order to provide the desired non-linear gradient, apparatus have been derived for automatically varying the proportion of two eluents. For example, in U.S. Pat. No. 3,446,057-Bakalyar et al a system is shown wherein a pair of motor-driven pumps are operated by a voltage supplied from a function generator. Systems such as that disclosed in the Bakalyar patent, while serving to advance the state of the art have been found to provide only fixed-length gradients whose overall characteristic has not only a predetermined shape, but a fixed time constant. If it is desired, for example, to provide an exponential eluent gradient which extends between two fixed non-terminal eluent ratios the exponential gradient is conventionally "switched in" at a desired initial point and then "switched out" at a termination point. This truncates the curve so that it starts and ends abruptly at "plateaus". It has been found that the latter approach substantially negates the value of the exponential curve, and moreover makes it impossible to duplicate the overall curve characteristic between differing initial and termination ratios or curve end points.

After a run is terminated the chromatograph system is conventionally reset by switching back to the original eluent which is used at the start of a run. In the example given above, this is done by switching from a 100% concentration of the first, initially-used eluent. This is usually accomplished by the simple expedient of opening or closing a valve so that the first eluent alone is allowed to flow. Recently it has been found that a sudden, abrupt "resetting" from one eluent to another is detrimental to at least some liquid chromatograph columns. It will accordingly be understood that it would be highly desirable to provide an elution gradient control system for effecting a curve of a desired configuration between varying initial and final eluent ratios; and for controlling the resetting time therebetween.

It is therefore an object of the present invention to provide an eluent control system for effecting a uniform gradient configuration between varying limits.

It is another object of the invention to provide an apparatus for achieving various gradient configurations over controllable time periods.

Another object is to provide a method for producing a consistent, repeatable eluent gradient which may be expanded or contracted without changing the overall shape thereof.

Still another object of the invention is to provide a control means for controllably resetting an eluent ratio from a final to an original value without damaging a chromatography column.

Still another object is to provide a method for returning an eluent composition from a final to an initial value along a predetermined exponential curve.

It is yet another object of the present invention to vary eluent composition along an exponential curve in a first time limit, and subsequently return the eluent composition to its initial state according to a similar controlled gradient, in a second, shorter period of time.

SUMMARY OF THE INVENTION

Briefly stated, according to one aspect of the invention the foregoing objects are achieved by providing a substantially linear, increasing signal extending between fixed limits, the slope of the signal being variable. A function generator is provided for receiving the signal and operating upon it in a predetermined manner to give rise to an exponential curve. The overall curve is multiplied by a compression factor determined by the end limits of the desired exponential gradient, and the resulting signal is algebraically combined with a signal representing the desired initial concentration of an eluent. The resulting gradient signal, which varies with time in a desired fashion, is then applied to appropriate eluent apportioning means, such as two or more pumps.

In a preferred embodiment, means are provided for resetting the eluent concentration to its original value by reversing the sense of the control signal and increasing the rate at which it is generated. The function generator continues to operate in its original mode to produce a "reset" control signal for returning the eluents to their original ratio along a gradient which is substantially a reflection of the original "run" gradient.

BRIEF DESCRIPTION OF THE DRAWINGS

While the specification concludes with claims particularly pointing out and distinctly claiming the subject matter which is regarded as the invention, it is believed that the invention will be better understood from the following description of a preferred embodiment taken in conjunction with the accompanying drawings in which:

DESCRIPTION OF A PREFERRED EMBODIMENT

Figure 1:
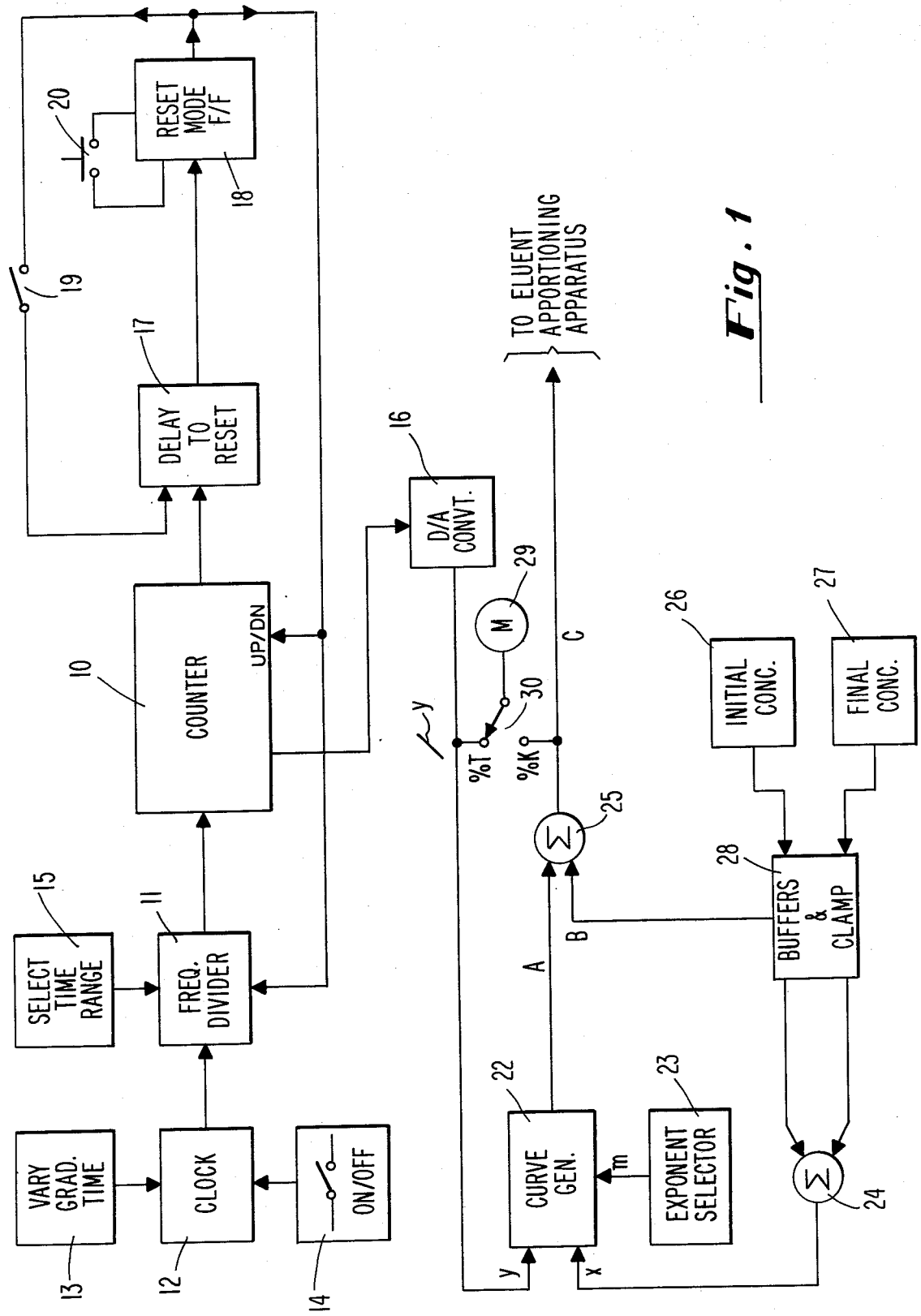
FIG. 1 is a functional schematic diagram illustrating the operation of the present invention.

As shown in FIG. 1, a digital counter 10 receives discrete pulses from a frequency divider 11 which in turn is responsive to pulses outputted by clock 12. The clock may comprise a variable frequency oscillator, so that the rapidity with which the pulses occur may be controlled. An appropriate control 13 serves to control the frequency or timing of clock 12 so as to vary the overall time of an eluent gradient to be produced. A switch 14 sets clock 12 into operation. Switch 14 may be operated either manually or automatically, although in a presently preferred embodiment a manual switch is used.

A second timing control 15 is provided for adjusting the time range of the gradient to be produced. The control 15 varies the effective divisor, or factor, by which pulses from clock 12 are divided by the frequency divider 11. Pulses having a thus-reduced rate are then fed to counter 10 which outputs signals to a digital-to-analog converter 16. When the counter has reached some predetermined maximum value, it outputs a termination signal to delay-to-reset stage 17. Depending upon the mode of operation, delay stage 17 may apply a reset signal to reset mode flip-flop 18. Flip-flop 18 then causes the counter to be actuated in the reverse direction in order to count down to its original, quiescent value. The mode of operation is determined by the state of switch 19; with the switch closed the system is in a "one shot" mode while when the switch is open the system is in the "auto" or repeating mode. Reset mode flip-flop 18 also applies an enabling signal to frequency divider 11. The latter signal causes the frequency divider to in effect apply a smaller divisor to the incoming clock signals thereby causing counter 10 to operate more rapidly in the reset or "down" direction. A reset switch 20 is also provided for manually causing flip-flop 18 to change modes.

As is familiar to those skilled in the art, digital-to-analog converter 16 produces a linearly-increasing pilot signal $y$ in response to the counts applied by counter 10. In fact, the output signal from converter 16 actually comprises a multiplicity of small, step-wise incremental changes; but the individual changes are insignificant for present purposes so that the signal produced by the converter can be considered to exhibit a linear change. Filters are provided in the preferred embodiment for smoothing the discontinuities in the output signal to further linearize the signal.

The pilot signal outputted by converter 16, herein denominated $y$, is applied to one input of function generator 22. The generator receives a second signal designated $m$ from a source 23, herein termed an exponent selector. A third input signal $x$ is derived from a summing junction 24 and applied to another input of generator 22.

In the presently preferred embodiment, function generator 22 operates upon signal $y$ according to some operator G to produce a function $G(y)$. In the preferred embodiment the operator serves to raise incoming signal $y$ to an exponential power $m$. Accordingly, $G(y) = y^m$. By varying the value of the output signal produced by exponent selector 23 the effective value of $m$, and thus the characteristic instantaneous slopes of $G(y)$, may be varied to suit a given application.

In addition, and of particular importance to the present invention, function generator 22 effectively multiplies the resultant signal $G(y)$ by a range factor $x$, represented by the signal derived from summing junction 24. In the depicted system junction 24 serves to subtract the applied signals and outputs a signal corresponding to the difference (algebraic sum). By multiplying the exponential function $G(y)$ by a constant value the instantaneous slopes, or curve, of the function remains identical while the range or end points of the function vary. Here it should be noted that while an exponential function may in theory be infinite in length, due to the finite duration of linear signal $y$ the exponential signal produced in response thereto has finite initial and terminal points. The corresponding end points or limits of $G(y)$ are expanded or contracted by the factor $x$, without causing any change in the shape of the curve.

The resulting signal A, herein defined as $$A = x \cdot G(y) = x \cdot y^m$$

is outputted by generator 22 and applied to a second summing junction 25 wherein it is algebraically combined with a signal B of a constant value.

The initial and final eluent concentrations are preset by means of adjustment stages 26, 27. The stages may comprise potentiometers or other sources of variable voltage. In the preferred embodiment, the signal denoting initial concentration is smaller than that denoting final concentration, the difference therebetween representing the range or "height" of the desired gradient. Signals representing the initial and final concentration are provided to a buffer and clamp stage 28, and passed to summing junction 24 wherein they are algebraically combined. The difference between the two values, herein denominated $x$, is then applied to function generator 22 to define the excursion or range of the desired exponential curve A. The provision of a clamp within the buffer and clamping stage 28 assures that signal $x$ can never be negative, i.e. it prevents the usable value of the final concentration signal from being less than that of the initial concentration signal. Signal B, which represents the desired initial concentration, forms the starting point or lower limit from which curve A arises. In a liquid chromatography control system, the value of B then represents the initial proportion of the eluents before a gradient is effected.

A meter 29 is provided, and coupled through switch 30 for selectively monitoring either the value of the linear signal $y$ outputted by converter 16, or the value of the eluent-controlling signal C arising at summing junction 25. Since the output of converter 16 always extends between predetermined limits, by displaying its value upon a properly-calibrated scale of meter 29 the percentage of the total signal value, and accordingly of elapsed gradient time, may be determined. Similarly, by noting the value of signal C the relative concentration of two known eluents may also be determined.

The control signal C, comprising the combination of the initial level signal and the gradient signal, is passed to eluent apportioning apparatus (not shown). The apportioning apparatus may comprise appropriate pumps, valving or the like, either alone or in combination with further signal processing or amplification circuitry. The apportioning apparatus serves to control the ratio of the two eluents in accordance with the instantaneous value of the conrol signal C.

In operation, the system of FIG. 1 is initially adjusted by selecting a value of exponent selector stage 23 which will give rise to a gradient curve of the desired configuration. If it is desired to automatically repeat the chromatographic analysis, switch 19 is closed and the delay-to-reset stage 17 is adjusted to provide the desired length of time between termination of the gradient and the end of the analyzing run. The time period during which the gradient is desired to occur is adjusted, in coarse form, by means of selector stage 15 and more precisely by means of gradient time adjustment 13. Finally the appropriate initial concentration of eluents is selected by setting the initial concentration adjustment 26. Energizing switch 14 is then closed and clock 12 begins to pulse at a rate determined by control 13. After the accrual of a predetermined number of pulses, in accordance with the adjustment of range selector 15, frequency divider 11 outputs a pulse to counter 10. Counter 10 responds to the pulses so received by outputting digital signals to digital-to-analog converter 16 to cause a linearly-increasing signal $y$ to be produced. As will now be understood, the more rapidly clock 12 operates, or the lower the effective divisor of frequency divider 11, the more rapidly counter 10 will count and accordingly the steeper will be the slope of signal $y$. Since the end points or limits of signal $y$ are constant, a steeper rise will result in the more rapid attainment of the upper limit. In this fashion a shorter, more rapid gradient may be produced.

Signal $y$ is then applied to function generator 22. Signal $x$, representing the range between initial and final eluent concentrations, is also applied to the function generator as is an exponent signal $m$. The resulting exponential signal A is then combined with the initial concentration signal B to control the concentration of the eluents being supplied to a chromatography system during a sample run. As will now be understood, the initial concentration or ratio of the eluents is determined by the setting of adjustment 26, with the final concentration being determined by the setting of stage 27.

The time period provided by the delay-to-reset stage 17 allows the flow of eluents to attain a predetermined, final concentration level and continue at this level until the delay-to-reset stage times out and triggers reset mode flip-flop 18. The signal outputted by the reset mode flip-flop is applied to counter 10 to cause it to count backwards ("down") to its original state. The same signal is also applied to frequency divider 11 and causes the latter to provide a lower effective divisor, increasing the rate at which pulses are fed to counter 10.

The net effect is to cause digital-to-analog converter 16 to output a linear signal whose slope is opposite in sense to the slope provided in the sample or non-reset mode of operation. In addition, the reversed slope is considerably steeper than during the sample run, owing to the increased counting rate. Since input signals $x$ and $m$ remain unchanged, a signal A is produced which has the same shape as that produced during the sample or run mode. Owing to the reversed, increased slope of the linear signal produced by converter 16, however, while signal A has the same curvature as before it takes the form of the reflection in time of the sample run gradient.

While the term "reflection in time" is not a recognized mathematical term, it will be used herein to describe the relationship between the "run" and the "reset" gradients. When the termination of the "run" gradient and the commencement of the "reset" gradient coincide at some time $t_m$ the gradients will comprise mirror images of one another reflected about time $t_m$ allowing, of course, for the fact that the "reset" gradient runs its course more quickly than does the "run" gradient. A more precise description of the relationship between the gradients is to say that the "run" and "reset" gradients exhibit identical slopes after identical proportions of their total times have elapsed, measuring from the points of termination and commencement, respectively.

As before, the gradient signal A is combined with an initial concentration signal B and applied to the apportioning apparatus. This time, however, the effect is to cause the various eluents to return to their original proportions. The rate of change or gradient of the eluents during the reset period, however, reflects the gradient provided during the sample or run period. Accordingly, an abrupt change in the eluent ratio does not occur. Abrupt changes in eluent ratios, such as may occur during conventional reset operations, are believed to injure columns used in liquid chromatographic apparatus. Accordingly, it has been found that by resetting the eluent concentrations in a non-instantaneous fashion such damage may be avoided. The present invention further provides means for resetting in which the reset gradient reflects the rates of change exhibited by the sample time gradient. If no damage to the column occurs from the use of a given sample run gradient, it is inferred that the reciprocal of the gradient, though occurring during a shorter time, will also not injure the column. Of course, the same holds true for linear gradients. With the disclosed apparatus the reset gradient will exhibit a slope which is greater than, but proportionate to, a linear run gradient.

Figure 2A:
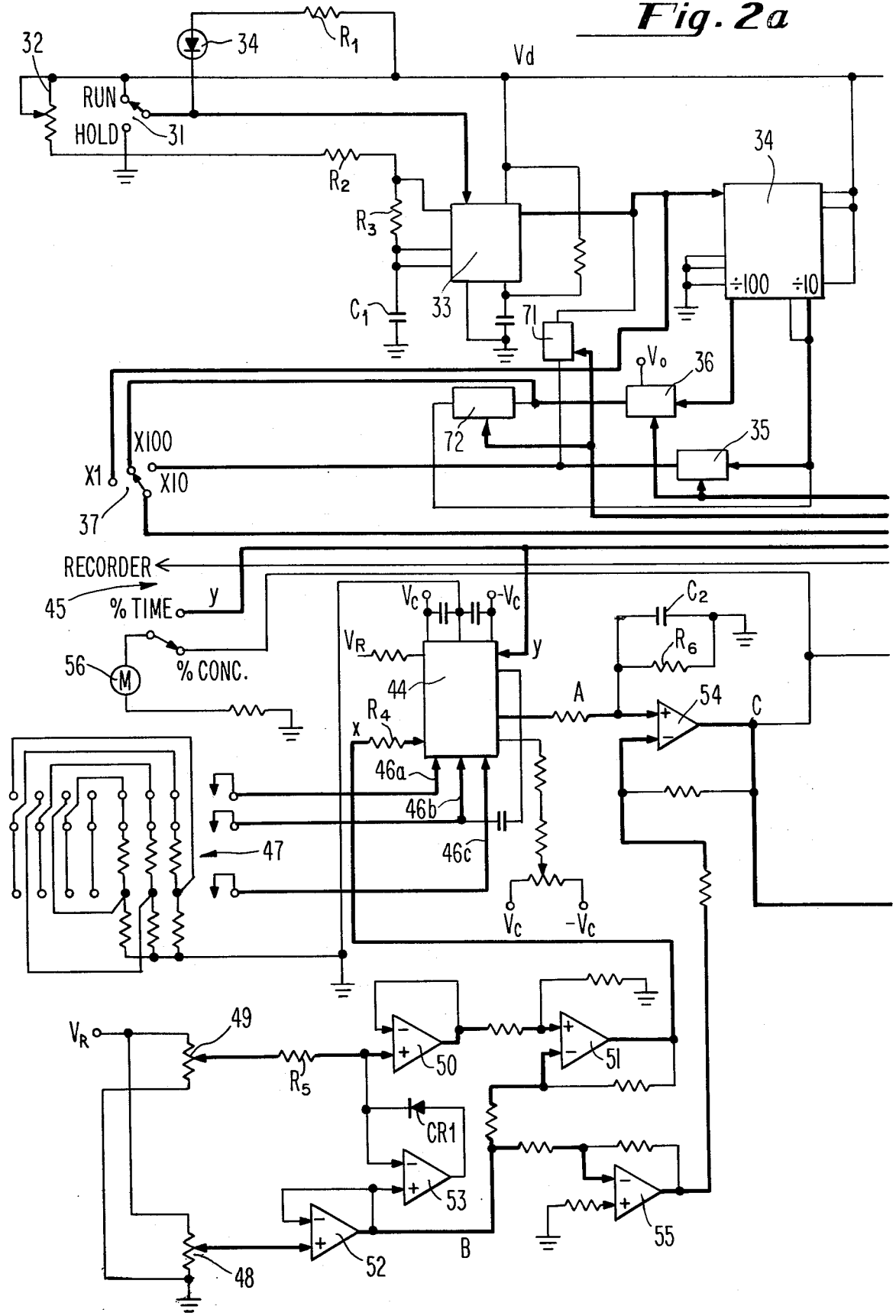
FIGS. 2a–2c comprise a circuit schematic diagram depicting a presently preferred embodiment of the invention.
Figure 2B:
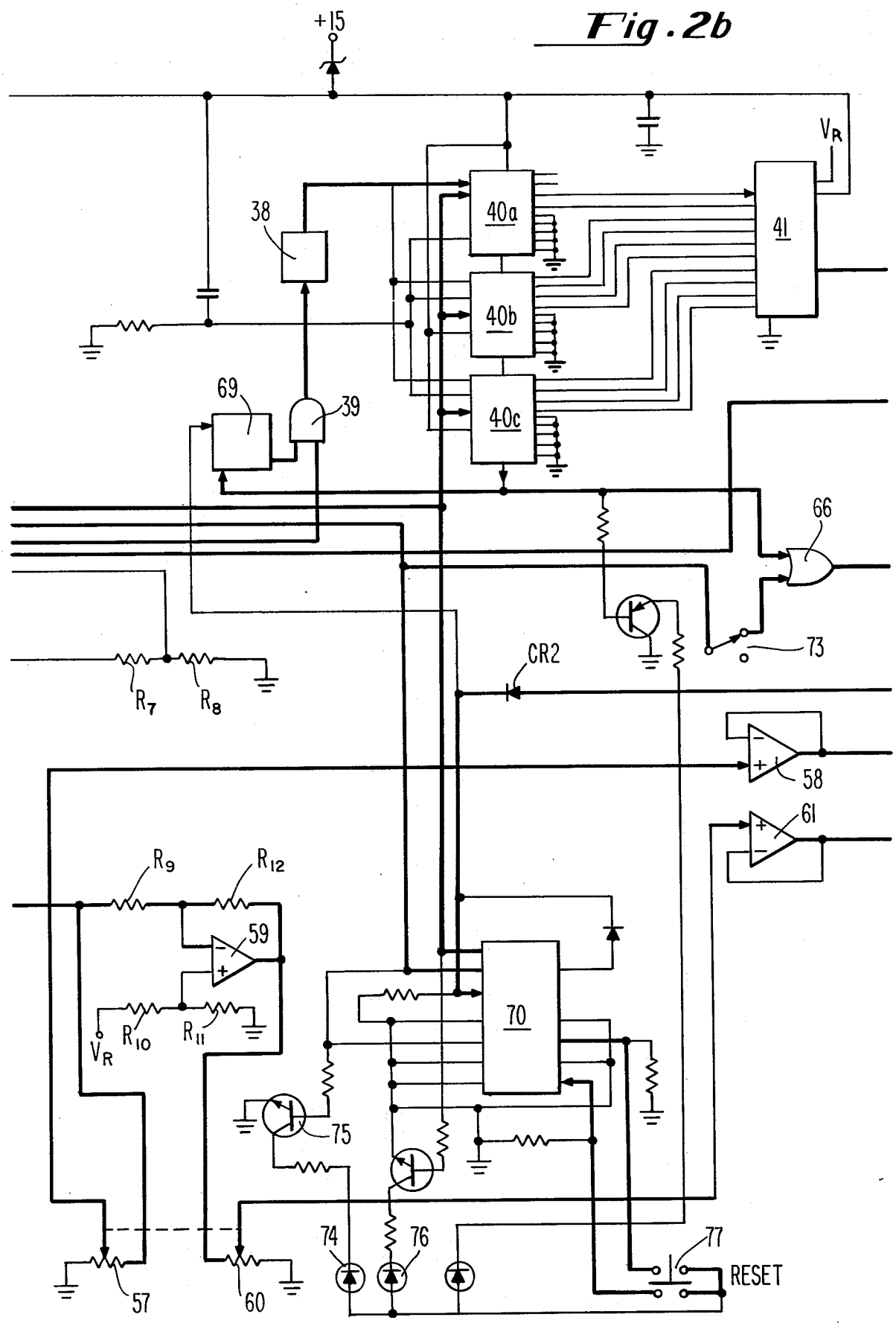
Figure 2C:
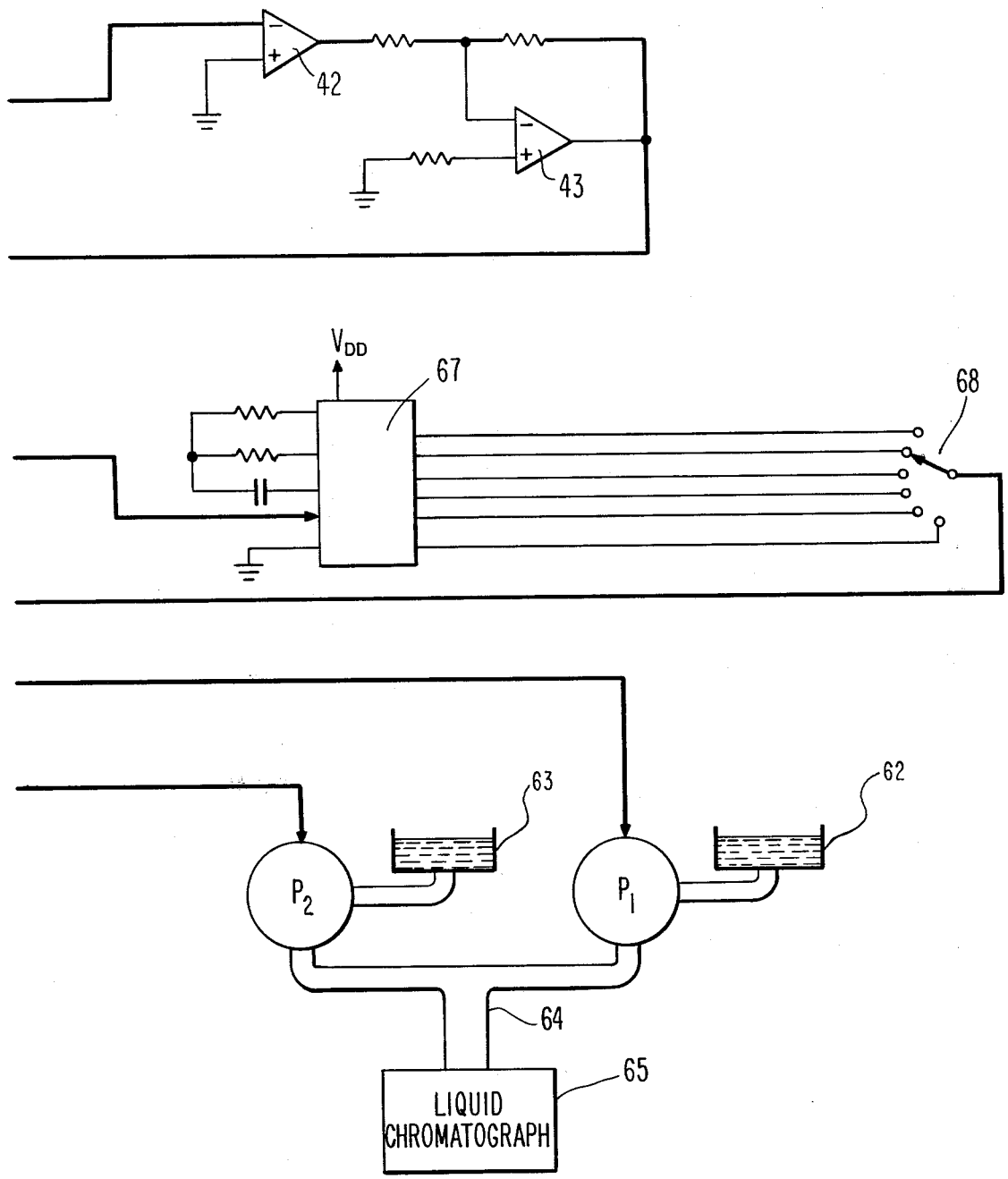

Turning now to FIGS. 2a-2c there is shown a schematic diagram which comprises a presently preferred embodiment of the invention. A switch 31, generally corresponding to switch 14 of FIG. 1, serves to selectively apply an energizing voltage to a clock stage 33. In a successfully tested embodiment the clock stage 33 comprised an integrated circuit of the type generally denominated 555, and which functions as a variable frequency oscillator.

It should herein be noted that, where appropriate, functional elements which correspond to common integrated circuits will be identified both functionally and by the industry designation number. While the latter number does not comprise an officially-sanctioned standard, it is well known by those skilled in the art that manufacturers of integrated circuits ordinarily adopt a common number for equivalent integrated circuit elements and prefix the number with an alphanumeric designation which indicates the identity of the manufacturer. As the source of manufacture is not relevant to the operation of most of the circuit elements of the present invention only the generic number will be used.

A visible indicator such as an LED 34 may be coupled to switch 31 to provide a readily apparent designation of switch status. A resistor $R_1$ limits current flow through the LED. Potentiometer 32, resistors $R_2$ and $R_3$ and capacitor $C_1$ determine the frequency of signals produced by clock stage 33. An appropriate voltage $V_d$ is provided to energize the circuit.

Clock pulses are thus outputted by clock stage 33 at a rate determined by the setting of potentiometer 32. The pulses are then applied to a digital frequency divider 34. The divider may comprise a 4518 integrated circuit, connected substantially as shown. The effective divisors provided by the divider 34 may advantageously be 10 and 100 so that the divider outputs pulses at 0.1 and 0.01 of the input or clock frequency. These outputs are applied to analog gates, 35, 36 respectively. The analog gates, comprising gated filed effect transistors disposed in a 4016 integrated circuit, serve as voltage-actuated switches for selectively applying the divided-frequency signal to a selector switch 37. Switch 37 corresponds to the time range selector 15 of FIG. 1, and in the depicted embodiment affords three positions for supplying outputted clock frequency, or factors thereof, to a counter 38 by way of AND gate 39. Counter 38 comprises a 4013 integrated circuit and divides the received, digital pulse train by a factor of two. In a successfully tested embodiment, the counter comprises a series of three 4516 integrated circuit counters 40a-40c connected in cascade to produce outputs on ten output lines, substantially as shown. The selected output gates count in binary form to a predetermined limit. The signals so derived are then applied to a digital-to-analog converter 41. The converter, advantageously a 7530 integrated circuit, acts in a manner familiar to those skilled in the art to produce a fine ascending "staircase" in response to the received binary signals. The "staircase" signal may for present purposes be regarded as a linearly-increasing output signal as the individual steps of the signal areinsignificant. The signal is pased through appropriate amplifiers 42, 43. The designated amplifiers comprise two of four such elements of a No. 324 integrated circuit. Amplifier 42 serves to convert output current from the converter to a usable voltage while amplifier 43 is connected to the preceding stage to comprise an analog inverter. The inversion of signal polarity is made necessary by the particular circuit arrangement of the preferred embodiment, however, and has no bearing upon the basic operation of the system. The linearly changing signal thus provided, hereinabove denominated pilot signals $y$, is applied to a function generator 44 which may advantageously comprise an integrated circuit No. 4302 analog function module manufactured by Burr-Brown, Inc. of Tuscon, Arizona. The signal is also supplied to one pole of a selector switch 45.

Function generator 44 is powered by complementary voltage source $+V_c$ and $-V_c$, and is also biased by reference voltage $V_r$, as shown. A plurality of inputs denominated 46a, 46b and 46c are derived from a resistor network 47. Network 47 may comprise a commercially available multiposition selector switch which serves to connect the various resistors in appropriate combinations, thus supplying various resistances between the input terminals 46a-46c. The impedances presented to the latter terminals determine the response of the function generator to the inputted signal $y$ and, in particular, determine the exponent $m$ to be applied to the incoming pilot signal. In this manner an exponential curve is generated whose characteristics are dependent both upon the slope of input signal $y$, and the valve of the exponent factor $m$. It will be apparent that exponential values of both above and below unity may be selected to afford convex or concave output functions; and that an exponent having an effective value of 1 may further be selected so that the signal outputted by the function generator approximates a straight line. It is believed, however, that in most practical applications it will be advantageous to use the present apparatus to derive signals for obtaining exponential gradients wherein gradient slope changes markedly within the range of interest.

A range signal $x$ is communicated to function generator 44 through current limiting resistor $R_4$. As will be demonstrated, signal $x$ denotes the difference between the initial and final concentration values and thus the limits between which an exponential gradient is desired.

First and second potentiometers 48, 49 are provided and coupled between a source of potential $V_r$, and ground to provide voltages defining the initial and final concentrations, respectively, which are desired. The final concentration voltage is coupled through resistor $R_5$ to an operational amplifier 50, connected as a buffer. The output of the buffer is supplied to the "positive" input terminal of a difference amplifier 51. The initial concentration signal derived from potentiometer 48 is coupled through a buffer 52 to the "negative" input terminal of difference amplifier 51. The buffer output is also applied to one terminal of an amplifier 53 having a diode $CR_1$ connected to provide a feedback loop thereabout. Amplifier 53 and diode $CR_1$ serve as a clamp for preventing a negative difference between the initial and final concentration signals from arising. The clamping circuit assures that the final concentration demanded by the system can never be less than the initial concentration of eluents.

Difference amplifier 51 provides the output signal $x$ which reflects the difference between the desired initial and final eluent concentrations. This difference then denotes the desired range over which the eluent gradient is to extend, and thus the end points or limits of the gradient curve. Function generator 44 then produces an output signal, herein denominated signal A, which may be defined by the relationship $$A = x \cdot y^m$$

It will be appreciated that the signal x, which represents the difference between initial and final concentrations, serves as a multiplying or scaling factor for compressing or expanding the range of the desired curve $y^m$. The actual curvature or progressive slope characterisitic of the curve remains unchanged despite variations in range so that successive runs may be repeated in which the initial and final concentration levels vary but which exhibit a common gradient characteristic. This attribute is of particular advantage in assuring that the separation of eluted peaks occurs in a consistent manner, despite changes in initial and final eluent concentrations.

An RC filter comprising resistor $R_6$ and capacitor $C_2$ smooths the resulting output signal, which is then applied to one input of a difference amplifier 54. The other input to the difference amplifier is derived through another amplifier 55, connected as an inverter and operative to supply a signal reflecting the negative of the desired initial eluent concentration. In the illustrated embodiment all of the variously-connected amplifiers 50–55 comprise No. 324 integrated circuits which are general-purpose operational amplifiers.

The initial concentration signal applied to the inverting terminal of differential amplifier 54 is herein designated signal B in the interests of consistency. Amplifiers 54 and 55 thus fulfill the function of summing junction 25 of FIG. 1. The output of amplifier 54, denominated signal C, is then the sum of signals A and B and so comprises an exponential gradient curve which is displaced upwardly by a constant value so as to provide an initial eluent concentration which later varies in a predetermined manner. The output signal C is coupled to selector switch 45 so that its value can be applied to a meter 56 for denoting the instantaneous percent of gradient, or relative eluent concentration. If desired, a signal for operating a recorder (not shown) may be derived from the intersection of a voltage divider comprising resistors $R_7$ and $R_8$.

It will be recognized that output signal C may be used directly to control the operation of appropriate eluent apportioning means such as a drive circuit for a pump, a solenoid valve, or the like. In one application of the present circuit, however, it was found desirable to process the signal still further. The signal is effectively split traversing a first potentiometer 57, from whence it flows through an output buffer 58 to a first pump $P_1$. The signal is also applied through a resistor $R_9$ to difference amplifier 59, connected substantially as shown. The positive input of the difference amplifier receives some proportion of reference voltage $V_n$ as determined by the relative valves of resistors $R_{10}$ and $R_{11}$. A feedback resistor $R_{12}$ is coupled between the output and the negative input terminal of the amplifier. The net effect of this arrangement is to provide an output voltage whose magnitude equals the difference between the instantaneous value of output signal C and the maximum possible value of outut signal C, so that at any given time the output of amplifier 59 added to the instantaneous value of output signal C gives a single, constant voltage.

The complementary output signal derived by amplifier 59 is coupled through a potentiometer 60 and buffering output amplifier 61 to a second pump $P_2$. The sliders of potentiometers 57, 60 are connected together so as to cause the potentiometers to operate in synchronism, assuring that the voltages applied to pumps $P_1$ and $P_2$ will "track" one another over the intended range of operation.

Pumps $P_1$ and $P_2$ are coupled to reservoirs 62 and 63 which contain first and second eluents, respectively. In a preferred embodiment pumps $P_1$ and $P_2$ comprise pumps manufactured by the Milton Roy Company of St. Petersburg, Florida and marketed under the proprietary designation "Constametric". Such pumps may generally be described as having the capability of providing either constant pressure or constant volume flow, and are admirably adapted for use with the present invention. By operating pumps $P_1$ and $P_2$ with complementary signals, as herein described, the total volume outputted by the pumps may be kept constant although the volume of each pump varies. The total eluent flow from the pumps is delivered by an appropriate manifold 64 to a liquid chromatograph 65 for sensing the above-referred to "peaks" of the sample under test.

The termination of the signal y which gives rise to the elution gradient is signaled by the state of counters 40a–40c. In particular, an "overflow" signal indicating that the maximum desired count has been attained is communicated from counter 40c to an OR gate 66. The gate then operates to energize a reset delay stage 67. Stage 67 may comprise a No. 4060 integrated circuit, which includes an internal oscillator and a timer or counter which energizes certain output terminals thereof at predetermined times. Ones of the terminals are coupled to various contacts of a selector switch 68. The slider of the selector switch is brought into contact with an output terminal of the delay stage which will provide an enabling signal after the desired period of time has elapsed. The signal thus outputted is then communicated by way of diode $CR_2$ to a flip-flop 69. The latter, which is advantageously a 4013 integrated circuit, then discontinues the enabling signal to AND gate 39. This effectively cuts off the flow of clock pulses to the digital counter. The enabling signal from switch 68 is also applied to a reset flip-flop 70, causing the latter to chagnge state and output a "RESET" signal which activates analog gates 71, 72. The RESET signal also flows through one-shot mode selector switch 73, when positioned as shown, to prevent the application of the "overflow" signal from counter 40c to delay stage 67. This prevents the commencement of a new gradient run when the reset operation is complete. With switch 73 open, however, this function cannot occur and so another delay-to-reset period is initiated at the end of the reset operation. At the ed of this period another "run" gradient will be automatically produced. If desired, the RESET signal may also be used to produce a visible signal such as from LED 74, driven by transistor 75. The illumination of LED 74 then denotes operation of the system of the RESET mode.

At the same time the RESET signal arises, a NOT-RESET signal is caused to cease through actuation of flip-flop 70. Accordingly, illumination of a "gradient mode" indicator LED 76 ceases, as does the signal enabling analog gates 35, 36. With gates 71, 72 and now enabled, the output of clock 33 is applied directly to the X1 input of selector switch 37. The ÷10 output of divider 34 is coupled to the X10 input by way of gate 36 and the ÷100 output coupled to the X100 input through gate 36. Accordingly, for the X1 range counters 40a–40c operate at a rate which is the same as for the gradient run. For the X10 and X100 ranges, however, the rate of operation is increased by a factor of 10. In addition, the application of the signal from flip-flop 70 to counters 40a–40c has the effect of causing the various counters to operate in reverse fashion, that is, to "count down". Finally, the signal serves to reset flip-flop 69 to enable gate 39 and allow clock pulses to be delivered to the counters. The net effect is to produce an output from digital-to-analog converter 41 which has a steep negative slope. Since function generator 44 remains in operation, all the other inputs thereto remaining unchanged, the function generator operates upon the new, reversely-directed linear signal $y$ to output a reset gradient signal A. Reset signal A is thus provided with a curvature or a characteristic which reflects the previous "run" gradient, but which runs its course in a substantially shorter time. The output signal is combined with an initial level signal B in the manner described above, and serves to drive pumps $P_1$ and $P_2$ in such a manner as to return the eluent composition to the original or initial state which obtained before the previous sample run.

It will now be seen that the inventive system allows a relatively short gradient time to be selected through appropriate adjustment of potentiometer 32 and/or selector switch 37. Resetting is automatic and a predetermined time period, selected by the setting of switch 68, is provided subsequent to the period of the accelerated reset gradient.

The present system also includes a manual reset capability which may be exercised by the operation of reset switch 77. When switch 77 is depressed it clocks flip-flop 70 and causes the system to immediately switch from the run to the reset mode, or vice versa.

Still another capability is provided by "one shot" switch 73. In "closed" mode, as shown in the Figure, signals are applied to OR gate 66 so that delay stage 67 will only become enabled at the end of a gradient run. With the switch open, delay stage 67 will be enabled at the end of both gradient and reset mode runs, and the system will continue to cycle automatically.

As will be evident from the foregoing description, certain aspects of the invention are not limited to the particular details of the examples illustrated, and it is therefore contemplated that other modifications or applications will occur to those skilled in the art. It is accordingly intended that the appended claims shall cover all such modifications and applications as do not depart from the true spirit and scope of the application.

What is claimed as new and desired to be secured by Letters Patent of the United States is:

1. Apparatus for varying the relative apportionment of a plurality of eluents flowing into a liquid chromatograph, comprising:
   means for generating a substantially linearly varying monotonic pilot signal extending between predetermined limiting values, including means for varying the slope of said pilot signal;
   means for providing a range signal $x$ representative of the intended variation in apportionment of the eluents;
   a function generator coupled to said means for generating for receiving said pilot signal $y$ and outputting a signal A in response thereto characterized by the expression
   $$A = x \cdot G(y)$$
   where G is an operator such that $G(y)$ is a monotonic function;
   means for selectively varying the value of $x$; and
   driver means coupled to said function generator for operating an eluent apportioning means to apportion the relative flow rates of ones of a plurality of eluents in accordance with the value of the outputted signal A.

2. Apparatus according to claim 1, where $G(y) = y^m$.

3. Apparatus according to claim 2, further including means for varying the value of $m$.

4. Apparatus for controllably varying the apportionment gradient between two eluents flowing into the column of a liquid chromatograph comprising:
   a first function generator for generating a substantially linear, monotonically varying pilot signal $y$ arising between predetermined limits;
   means for varying the slope of said pilot signal whereby said pilot signal may be caused to arise between said limits in a lesser or greater time period;
   a second function generator coupled to said first function generator for receiving said pilot signal $y$ and outputting a signal A in response thereto, said signal A having upper and lower limits and characterized by the expression
   $$A = x \cdot G(y)$$
   where G is an operator such that $G(y)$ is a monotonic non-linear function and $x$ is a predetermined constant value, said second function generator comprising means for selectively varying the value of $x$ to thereby vary the difference between the upper and lower limits of signal A; and
   eluent apportioning means coupled to said function generator and responsive to said outputted signal A for varying the proportion of two eluents.

5. Apparatus as defined in claim 4, further including means coupled to said second function generator and to said eluent apportioning means for adding a constant signal B to said output signal A.

6. Apparatus as defined in claim 5 wherein said means for adding comprises first means for adjustably determining a first signal;
   second means for generating a second signal;
   means for combining said second signal with said output signal A;
   means for deriving the difference between said first and said second voltages to provide a difference signal $x$; and
   means for applying said signal $x$ to said second function generator;
   whereby the range of the signal A outputted by said second function generator is expanded in accordance with a change in the value of the signal $x$.

7. A control system for effecting a non-linear gradient between two eluents in a liquid chromatograph and for selectively expanding and contracting the range of the gradient without varying the shape thereof, comprising:
   a clock stage for producing clock pulses;
   means for adjustably varying the rate of said clock pulses;
   a counter receiving said clock pulses and producing a digital output signal in response thereto;
   a digital-to-analog converter for converting said digital signal into an analog pilot signal $y$ extending between predetermined limits;
   means for producing a first signal representing a desired initial eluent ratio;
   means for producing a second signal representing a desired final eluent ratio;

first summing means for receiving said first and said second signals and outputting a range signal x representative of the difference therebetween;

a function generator responsive to said pilot signal y and said range signal x to output gradient signal A where $$A = x \cdot y^m$$

said function generator including means for varying the effective value of m; and means for combining said gradient signal A with said first signal.

8. A control system as defined in claim 7, further including:

reset means coupled to said counter and responsive thereto for causing said counter to operate in a reverse mode after attaining a predetermined, maximum value;

said reset means further being coupled to said clock stage for increasing the rate at which clock pulses are applied to said counter.

9. A system for controlling the gradient between two eluents in a liquid chromatograph, comprising:

function generator means for producing a first, non-linear signal over a given range during a first, run period;

control means responsive to said signal for determining the instantaneous ratio of the eluents; and means for causing said function generator means to produce a second non-linear signal over said given range during a second, reset period which is shorter than said run period.

10. A system as defined in claim 9, wherein said first and second non-linear signals are exponential in form.

11. A system as defined in claim 9, wherein said second non-linear signal exhibits a characteristic slope which is substantially a reflection in time of the characteristic slope of said first signal.

12. A method for controlling the ratio between two eluents in a chromatograph system, comprising:

developing a periodic, digital signal which arises at a determinable rate;

converting said digial signal to a substantially linearly-increasing analog signal y which extends between fixed limits;

operating upon said substantially linearly-increasing signal y with an operator G to produce a non-linear signal G(y);

developing a range signal x representing a desired gradient range;

multiplying said non-linear signal by said range signal to produce a gradient signal A; and varying the ratio between the two eluents from an initial to a final concentration in response to the instantaneous value of gradient signal A.

13. A method as defined in claim 12, further including the step of adding a constant signal B to said gradient signal to determine the initial ratio of the eluents.

14. A method as defined in claim 13, wherein said signal G(y) is characterized by the expression $$G(y) = y^m$$

15. A method as defined in claim 12, further including the steps of:

increasing the rate at which said periodic, digital signal arises;

converting said digital signal to a substantially linearly-decreasing signal y which extends between fixed limits;

operating upon said substantially linearly-decreasing signal y with an operator to produce a reset gradient signal having a finite slope; and varying the ratio between the two eluents from said final to said initial concentration in response to the instantaneous value of the reset gradient signal.

16. A method as defined in claim 15, wherein said linearly-decreasing signal y is operated upon by said operator G(y).

17. A method as defined in claim 16, wherein said operator G(y) is characterized by the expression $$G(y) = y^m$$

* * * * *

UNITED STATES PATENT AND TRADEMARK OFFICE
CERTIFICATE OF CORRECTION

PATENT NO. : 4,066,879
DATED : January 3, 1978
INVENTOR(S) : Brian E. Leaver et al It is certified that error appears in the above-identified patent and that said Letters Patent are hereby corrected as shown below:

Col. 7, line 39, "filed" should be --field--;

" line 61, "pased" should be --passed--.

Col. 9, line 59, "outut" should be --output--.

Col. 10, line 41, "chagnge" should be --change--;

" line 50, "ed" should be --end--.

Col. 12, line 63, after "tal" the word --output-- should be inserted.

Col. 14, line 3, "digial" should be --digital--.

Signed and Sealed this

Twenty-seventh Day of June 1978

[SEAL]

Attest:

RUTH C. MASON
Attesting Officer

DONALD W. BANNER
Commissioner of Patents and Trademarks